United States Patent [19]

Watanabe et al.

[11] Patent Number: 4,623,741
[45] Date of Patent: Nov. 18, 1986

[54] CHLOROSILANE COMPOUNDS

[75] Inventors: Junichiro Watanabe; Yuichi Funahashi, both of Ohta, Japan

[73] Assignee: Toshiba Silicone Co., Ltd., Tokyo, Japan

[21] Appl. No.: 822,979

[22] Filed: Jan. 24, 1986

[30] Foreign Application Priority Data

Mar. 26, 1985 [JP] Japan .................. 60-61260

[51] Int. Cl.⁴ ............................. C07F 7/08
[52] U.S. Cl. ................................... 556/465
[58] Field of Search ......................... 556/465

[56] References Cited

U.S. PATENT DOCUMENTS 4,297,499 10/1981 Koga et al. .................. 556/465
4,408,017 10/1983 Martin ..................... 556/465 X

*Primary Examiner*—Paul F. Shaver

[57] ABSTRACT

An ethylidenenorbornyl group-containing chlorosilanes compound represented by the general formula:

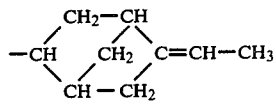

wherein $R^1$ stands for a saturated or unsaturated monovalent hydrocarbon group of 1 to 8 carbon atoms, Y for

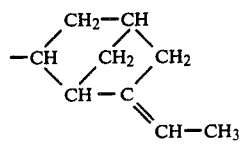

or a for an integer of the value of 1 to 3, b for an integer of the value of 0 to 2, and a+b for an integer of the value of 1 to 3.

1 Claim, 3 Drawing Figures

CHLOROSILANE COMPOUNDS

The present application claims priority of Japanese Patent Application Ser. No. 85/61260 filed on Mar. 26, 1985.

BACKGROUND OF THE INVENTION

This invention relates to novel and useful chlorosilane compounds containing an ethylidenenorbornyl group.

While various species of carbon functional chlorosilanes are used as silane coupling agents and as intermediates for various silane compounds or siloxane compounds, chlorosilanes which are in the form of a condensed ring and are possessed of an unsaturated group have never been known to the art.

SUMMARY OF THE INVENTION

The inventors have made a diligent study in search of chlorosilanes which are in the form of a condensed ring and are possessed of an unsaturated group. They have consequently perfected this invention.

Specifically, this invention relates to an ethylidenenorbornyl group-containing chlorosilane compound represented by the general formula:

$$Y_a(R^1)_b Si(Cl)_{4-a-b}$$

wherein $R^1$ stands for a saturated or unsaturated monovalent hydrocarbon group of 1 to 8 carbon atoms, Y for

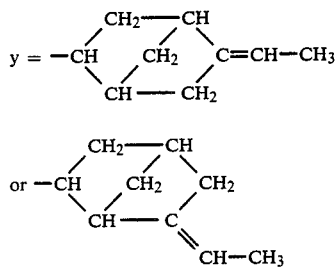

a for an integer of the value of 1 to 3, b for an integer of the value of 0 to 2, and a+b for an integer of the value of 1 to 3.

DESCRIPTION OF THE INVENTION

Illustrative of the saturated or unsaturated monovalent hydrocarbon groups of 1 to 8 carbon atoms represented by $R^1$ in the general formula mentioned above, there may be cited alkyl groups such as methyl group, ethyl group, propyl group, butyl group, pentyl group, hexyl group, heptyl group, and octyl group; alkenyl groups such as vinyl group and allyl group; aryl groups such as phenyl group and tolyl group; aralkyl groups such as benzyl group and β-phenylethyl group; and groups having a 3,3,3-trifluoropropyl group, cyano radical, a halogen atom, or the like partially substituted for the hydrogen atoms bonded to the carbon atoms of the monovalent hydrocarbon groups mentioned above.

Typical ethylidenenorbornyl group-containing chlorosilane compounds of the present invention are cited below. It is provided that the symbol Y has the same meaning as defined above. For the sake of simplicity, the following symbols will be used; Me for methyl group, Et for ethyl group, and Ph for phenyl group.

$YSiCl_3$,
$Y(Me)SiCl_2$,
$Y(Me)_2SiCl$,
$Y(Me)(Ph)SiCl$,
$Y_2SiCl_2$,
$Y(Ph)SiCl_2$

These ethylidenenorbornyl group-containing chlorosilane compounds can be synthesized by using, as starting materials, chlorosilanes possessing a hydrogen atom bonded to a silicon atom and 5-ethylidene-bicyclo(2,2,1)hept-2-ene. The desired compound is obtained by causing a given chlorosilane to undergo addition reaction with 5-ethylidenebicyclo(2,2,1)hept-2-ene, used desirably in an equivalent weight relative to the mols of the Si—H bond of the chlorosilane, in the presence of a platinum compound such as chloroplatinic acid as a catalyst.

EXAMPLES OF THE INVENTION

Now, the present invention will be described with reference to working examples. Wherever "parts" are mentioned, they are meant as "parts by weight."

EXAMPLE 1

In a flask provided with a dropping funnel, 100 parts of 5-ethylidene-bicyclo(2,2,1)hept-2-ene and 0.02 part of chloroplatinic acid added as a catalyst were heated to 30° C. Then, 90 parts of methyldichlorosilane were gradually added dropwise through the dropping funnel to the mixture in the flask. The system was kept in a refluxed state and the liquid temperature was gradually raised as the reaction progressed. The addition reaction was continued for 20 hours, with the liquid temperature kept at 80° C.

The reaction mixture so obtained was heated at 70° C. under a vacuum (8 mmHg) to be stripped off raw materials. By distilling the residue, there was obtained 150 parts (79% in yield) of a 1:1.1 mixture of the compounds (a) and (b) represented by the following formulas:

wherein

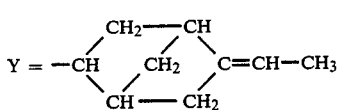 (a)

and

wherein $$Y = -CH \underset{CH}{\overset{CH_2-CH}{\diagdown}} \underset{C}{\overset{CH_2}{\diagup}} \underset{CH-CH_3}{\overset{CH_2}{\diagdown}} \quad (b)$$

| Boiling point | 98° C./8 mmHg |
| --- | --- |
| Refractive index ($n_D^{25}$) | 1.499 |
| Specific gravity (25° C.) | 1.107 |
| Molecular weight | 235 |
| | (gas-mass spectral analysis) |

Figure 1:
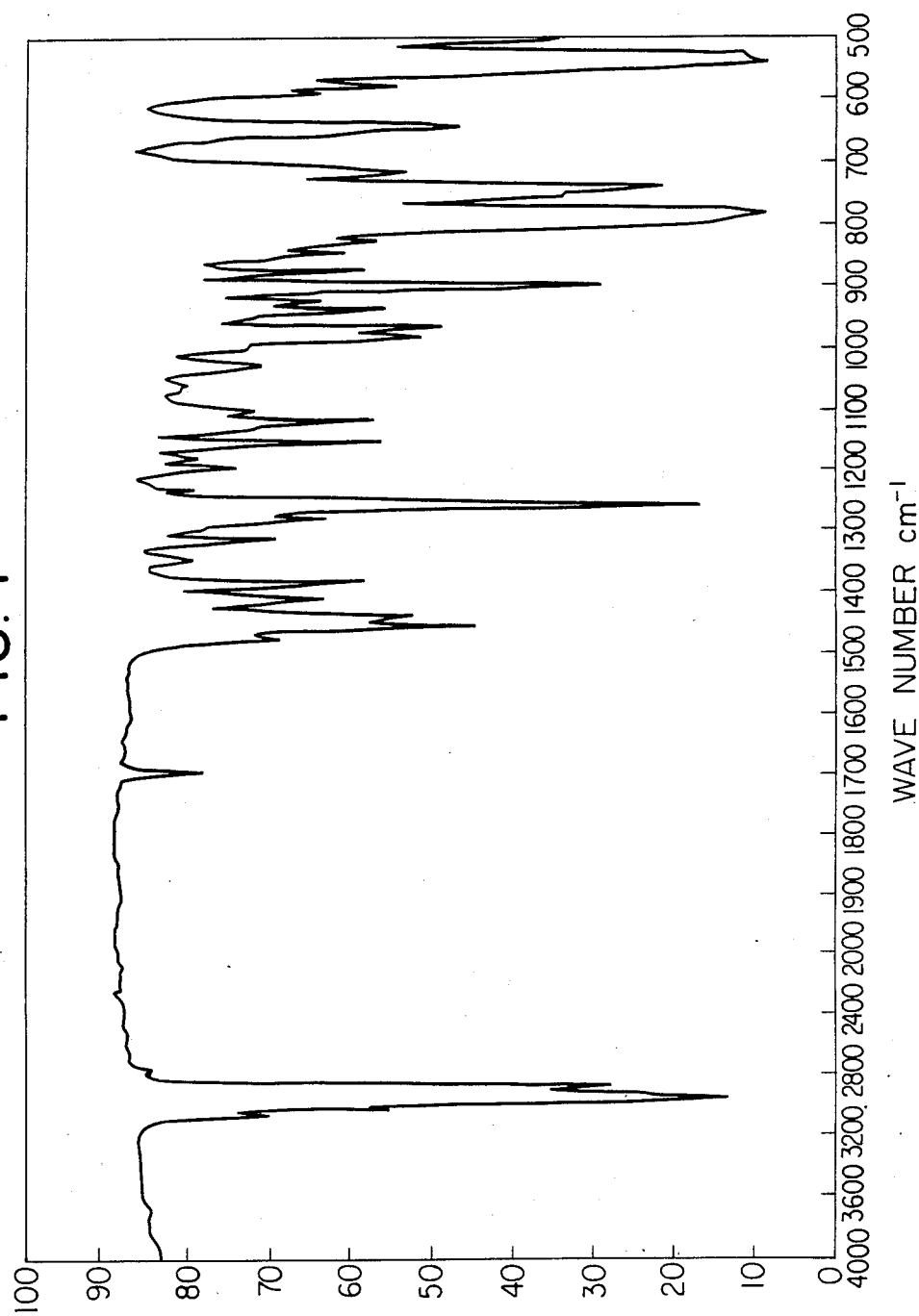
FIG. 1, FIG. 2, and FIG. 3 are infrared absorption spectra of the mixtures obtained respectively in Example 1, Example 2, and Example 3.
Figure 2:
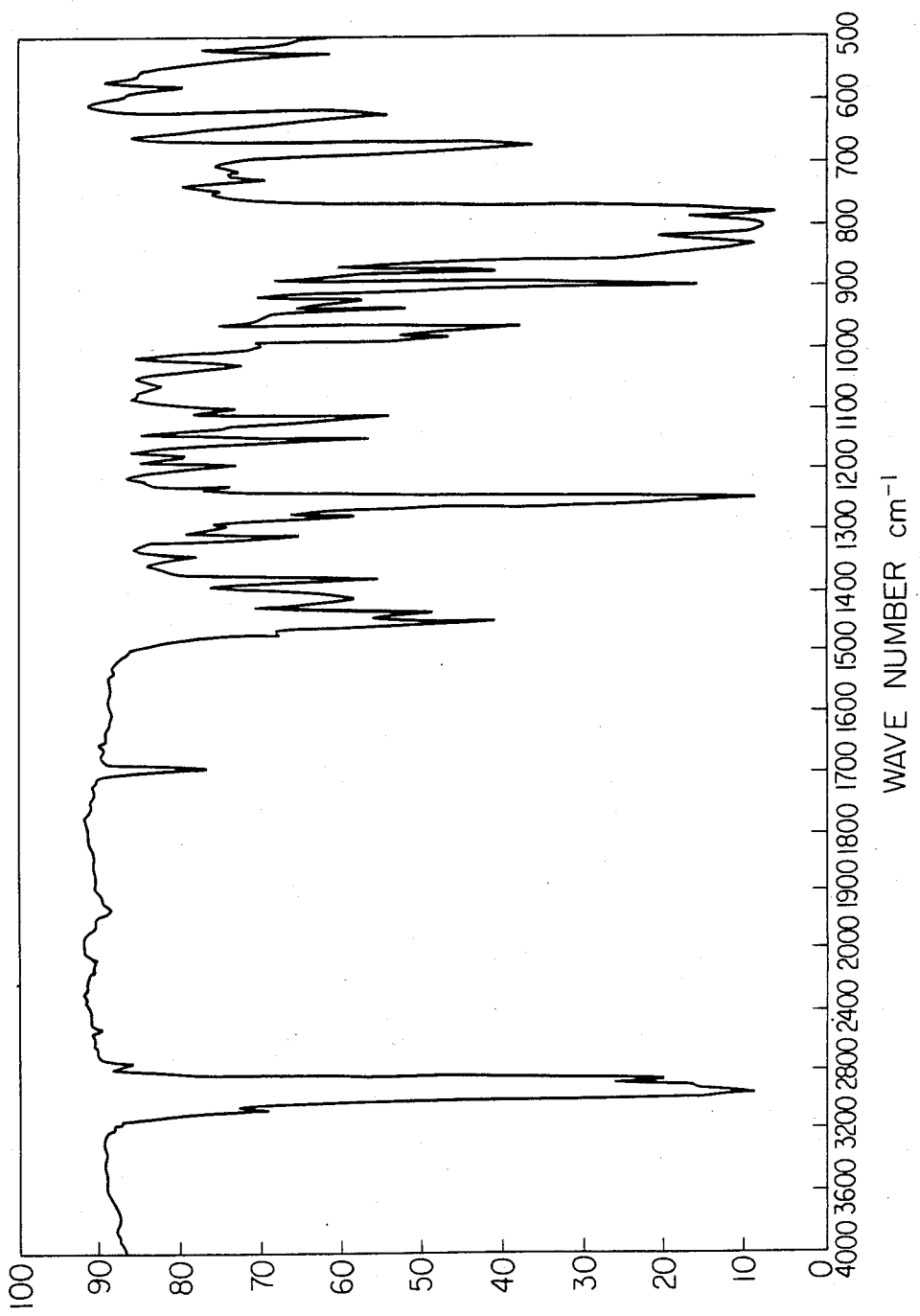
Figure 3:
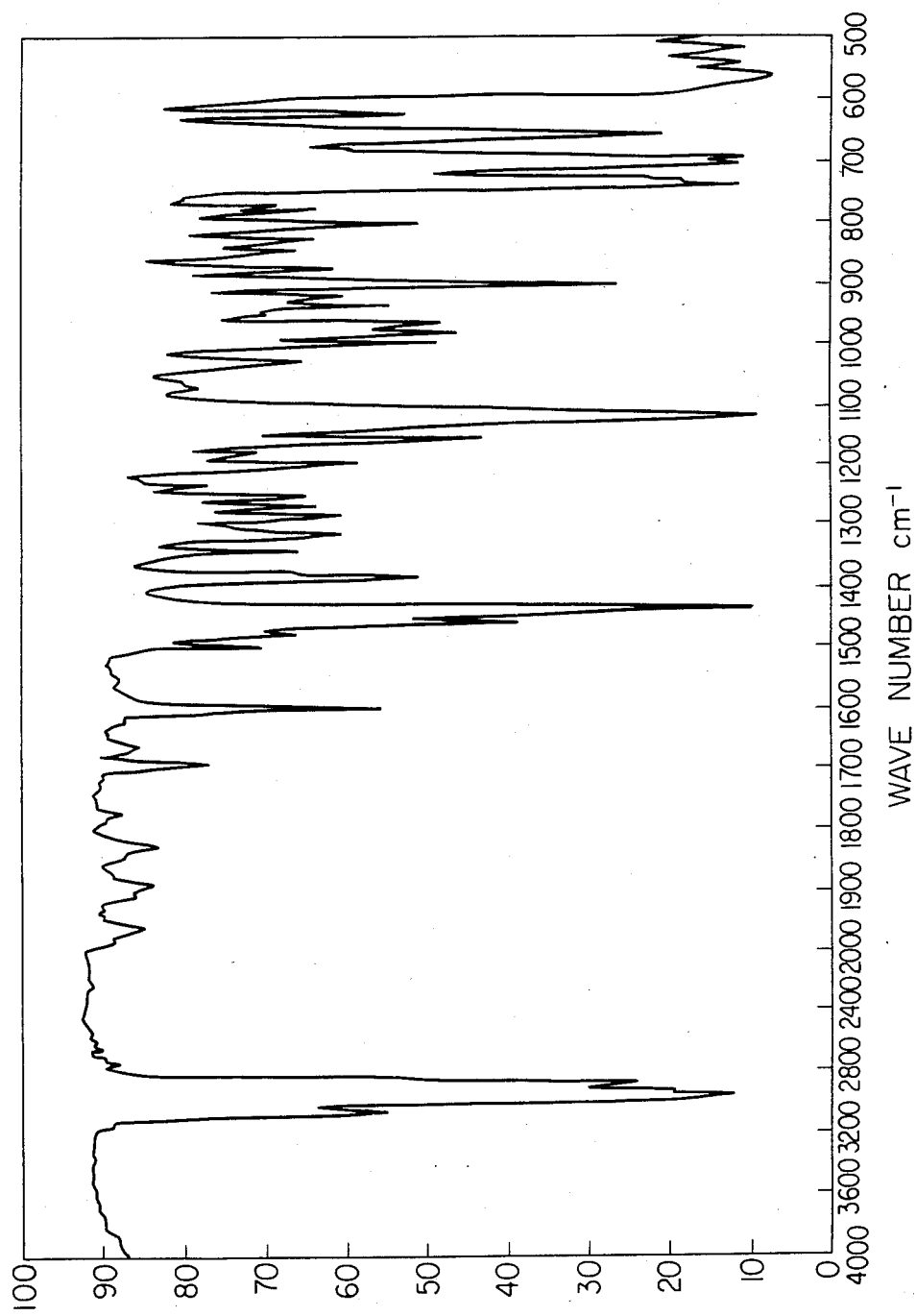

| | Elementary analysis | |
| --- | --- | --- |
| | Found | Calculated (as $C_{10}H_{16}Cl_2Si$) |
| C | 51.5 | 51.1 |
| H | 7.2 | 6.9 |
| Cl | 29.8 | 30.1 |
| Si | 11.5 | 11.9 |
| Infrared absorption spectrum FIG. 1 | | |

EXAMPLE 2

In a flask provided with a dropping funnel, 100 parts of 5-ethylidene-bicyclo(2,2,1)hept-2-ene and 0.02 part of chloroplatinic acid added as a catalyst were heated to 30° C. Then, 75 parts of dimethylchlorosilane were gradually added dropwise through the dropping funnel to the mixture in the flask. The system was kept under a refluxed state and the liquid temperature was gradually raised as the reaction progressed. The addition reaction was continued for 20 hours, with the liquid temperature kept at 80° C.

The reaction mixture so obtained was heated at 70° C. under a vacuum (10 mmHg) to be stripped off raw materials. By distilling the residue, there was obtained 150 parts (86% in yield) of a 1:1.1 mixture of the compounds (c) and (d) represented by the following formulas:

$$Y-\underset{Me}{\overset{Me}{\underset{|}{Si}}}-Cl$$

wherein $$Y = -CH \underset{CH}{\overset{CH_2-CH}{\diagdown}} \underset{CH_2}{\overset{CH_2}{\diagup}} C=CH-CH_3 \quad (c)$$

and $$Y-\underset{Me}{\overset{Me}{\underset{|}{Si}}}-Cl$$

wherein $$Y = -CH \underset{CH}{\overset{CH_2-CH}{\diagdown}} \underset{C}{\overset{CH_2}{\diagup}} \underset{CH-CH_3}{\overset{CH_2}{\diagdown}} \quad (d)$$

| Boiling point | 97° C./10 mmHg |
| --- | --- |
| Refractive index ($n_D^{25}$) | 1.491 |
| Specific gravity (25° C.) | 0.992 |
| Molecular weight | 214.5 |
| | (gas-mass spectral analysis) |

| | Elementary analysis | |
| --- | --- | --- |
| | Found | Calculated (as $C_{11}H_{19}ClSi$) |
| C | 61.2 | 61.5 |
| H | 9.2 | 8.9 |
| Cl | 16.3 | 16.5 |
| Si | 13.3 | 13.1 |

EXAMPLE 3

In a flask provided with a dropping funnel, 100 parts of 5-ethylidene-bicyclo(2,2,1)hept-2-ene and 0.02 part of chloroplatinic acid added as a catalyst were heated to 80° C. Then, 140 parts of phenyldichlorosilane were gradually added dropwise through the dropping funnel to the mixture. The system was kept under a refluxed state and the liquid temperature was gradually raised as the reaction progressed. The addition reaction was continued for 20 hours, with the liquid temperature kept at 140° C.

The reaction mixture so obtained was heated at 120° C. under a vacuum (8 mmHg) to be stripped off raw materials. By distilling the residue, there was obtained 200 parts (83% in yield) of a 1:1.1 mixture of the compounds (e) and (f) represented by the following formulas:

$$Y-\underset{Cl}{\overset{C_6H_5}{\underset{|}{Si}}}-Cl$$

wherein $$Y = -CH \underset{CH}{\overset{CH_2-CH}{\diagdown}} \underset{CH_2}{\overset{CH_2}{\diagup}} C=CH-CH_3 \quad (e)$$

$$Y-\underset{Cl}{\overset{C_6H_5}{\underset{|}{Si}}}-Cl$$

wherein $$Y = -CH \underset{CH}{\overset{CH_2-CH}{\diagdown}} \underset{C}{\overset{CH_2}{\diagup}} \underset{CH-CH_3}{\overset{CH_2}{\diagdown}} \quad (f)$$

| Boiling point | 168° C./6 mmHg |
| --- | --- |
| Refractive index ($n_D^{25}$) | 1.552 |
| Specific gravity (25° C.) | 1.155 |
| Molecular weight | 297 |
| | (gas-mass spectral analysis) |

$$Y = -\overset{CH_2-CH}{\underset{CH-C}{CH\underset{}{\phantom{X}}CH_2\underset{}{\phantom{X}}CH_2}}\diagdown_{CH-CH_3} \quad (f)$$

| Elementary analysis | | |
|---|---|---|
| | Found | Calculated (as $C_{15}H_{18}Cl_2Si$) |
| C | 60.4 | 60.4 |
| H | 6.4 | 6.1 |
| Cl | 23.8 | 23.9 |
| Si | 9.4 | 9.4 |

EXAMPLE 4

In a flask provided with a dropping funnel, 100 parts of 5-ethylidene-bicyclo(2,2,1)hept-2-ene and 0.02 part of chloroplatinic acid added as catalyst were heated to 30° C. Then, 105 parts of trichlorosilane were gradually added dropwise through the dropping funnel to the mixture in the flask. The system was kept under a refluxed state and the liquid temperature was gradually raised as the reaction progressed. The addition reaction was continued for 50 hours, with the temperature kept at 80° C.

The reaction mixture so obtained was heated at 70° C. under a vacuum (8 mmHg) to be stripped off raw materials. By distilling the residue, there was obtained 100 parts (49% in yield) of a 1:1.1 mixture of the compounds (g) and (h) represented by the following formulas:

wherein

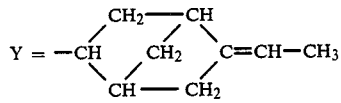  (g)

and

wherein $$Y = -\overset{CH_2-CH}{\underset{CH-C}{CH\underset{}{\phantom{X}}CH_2\underset{}{\phantom{X}}CH_2}}\diagdown_{CH-CH_3} \quad (h)$$

| Boiling point | 147° C./10 mmHg |
|---|---|
| Refractive index ($n_D{}^{25}$) | 1.505 |
| Specific gravity (25° C.) | 1.266 |
| Molecular weight | 255.5 |
| | (gas-mass spectral analysis) |

| Elementary analysis | | |
|---|---|---|
| | Found | Calculated (as $C_9H_{13}Cl_3Si$) |
| C | 42.5 | 42.3 |
| H | 4.7 | 5.1 |
| Cl | 41.8 | 41.6 |
| Si | 11.0 | 11.0 |

The ethylidenenorbornyl group-containing chlorosilanes compounds of the present invention can be used as silane coupling agents, as intermediates for alkoxysilanes or siloxanes, or as surface treating agents for fillers in rubber compounds.

We claim:

1. An ethylidenenorbornyl group-containing chlorosilane compound represented by the general formula:

$$Y_a(R^1)_b Si(Cl)_{4-a-b}$$

wherein $R^1$ stands for a saturated or unsaturated monovalent hydrocarbon group of 1 to 8 carbon atoms, Y for

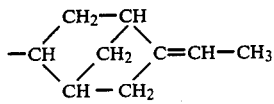

or

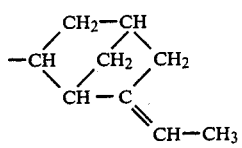

a for an integer of the value of 1 to 3, b for an integer of the value of 0 to 2, and a+b for an integer of the value of 1 to 3.

* * * * *